(12) United States Patent
West et al.

(10) Patent No.: US 7,524,672 B2
(45) Date of Patent: Apr. 28, 2009

(54) MICROFLUIDIC MICROARRAY SYSTEMS AND METHODS THEREOF

(75) Inventors: Jay A. A. West, Castro Valley, CA (US); Kyle W. Hukari, San Ramon, CA (US); Gary A. Hux, Tracy, CA (US)

(73) Assignee: Sandia Corporation, Livermore, CA (US)

( * ) Notice: Subject to any disclaimer, the term of this patent is extended or adjusted under 35 U.S.C. 154(b) by 731 days.

(21) Appl. No.: 10/946,920

(22) Filed: Sep. 22, 2004

(65) Prior Publication Data

US 2006/0063160 A1    Mar. 23, 2006

(51) Int. Cl.
C12M 1/34 (2006.01)
C12M 3/00 (2006.01)

(52) U.S. Cl. .................................. 435/287.2

(58) Field of Classification Search .... 435/287.2–288.5
See application file for complete search history.

(56) References Cited

U.S. PATENT DOCUMENTS

| | | | |
|---|---|---|---|
| 4,908,112 A | 3/1990 | Pace | 204/299 |
| 5,061,336 A | 10/1991 | Soane | 156/245 |
| 5,071,531 A | 12/1991 | Soane | 204/616 |
| 5,132,012 A | 7/1992 | Miura et al. | 210/198.2 |
| 5,135,627 A | 8/1992 | Soane | 204/455 |
| 5,194,133 A | 3/1993 | Clark et al. | 208/299 |
| 5,569,364 A | 10/1996 | Hooper et al. | 204/455 |
| 5,571,410 A | 11/1996 | Swedberg et al. | 210/198.2 |
| 5,580,990 A | 12/1996 | Van den Berg et al. | 549/212 |
| 5,605,662 A | 2/1997 | Heller et al. | |
| 5,631,337 A | 5/1997 | Sassi et al. | 526/307.2 |
| 5,770,365 A | 6/1998 | Lane et al. | 435/6 |
| 5,800,690 A | 9/1998 | Chow et al. | 204/451 |
| 5,824,204 A | 10/1998 | Jerman | 204/601 |
| 5,929,208 A | 7/1999 | Heller et al. | 530/333 |
| 6,001,229 A | 12/1999 | Ramsey | 204/451 |
| 6,017,696 A | 1/2000 | Heller | 435/6 |
| 6,051,380 A | 4/2000 | Sosnowski et al. | 435/6 |
| 6,133,038 A | 10/2000 | Houthoff et al. | 436/84 |
| 6,210,896 B1 | 4/2001 | Chan | 435/6 |
| 6,238,624 B1 | 5/2001 | Heller et al. | 422/68.1 |
| 6,245,508 B1 | 6/2001 | Heller et al. | 435/6 |
| 6,258,606 B1 | 7/2001 | Kovacs | 436/149 |
| 6,270,641 B1 | 8/2001 | Griffiths et al. | 204/451 |
| 6,284,117 B1 | 9/2001 | Smolko et al. | 204/543 |
| 6,290,909 B1 | 9/2001 | Paul et al. | 422/70 |

(Continued)

FOREIGN PATENT DOCUMENTS

EP    1 385 006 A2    1/2004

(Continued)

OTHER PUBLICATIONS

U.S. Appl. No. 10/701,097, filed Nov. 4, 2003, Jason West.

(Continued)

*Primary Examiner*—Walter D Griffin
*Assistant Examiner*—Shanta G Doe
(74) *Attorney, Agent, or Firm*—Woodcock Washburn LLP

(57) ABSTRACT

Disclosed are systems that include a manifold in fluid communication with a microfluidic chip having a microarray, an illuminator, and a detector in optical communication with the microarray. Methods for using these systems for biological detection are also disclosed.

30 Claims, 11 Drawing Sheets

U.S. PATENT DOCUMENTS

| | | | |
|---|---|---|---|
| 6,309,601 B1 | 10/2001 | Juncosa et al. | 422/68.1 |
| 6,315,953 B1 | 11/2001 | Ackley et al. | 422/68.1 |
| 6,316,608 B1 | 11/2001 | Reynolds et al. | 536/22.1 |
| 6,355,420 B1 | 3/2002 | Chan | 435/6 |
| 6,403,311 B1 | 6/2002 | Chan | 435/6 |
| 6,403,367 B1 | 6/2002 | Cheng et al. | 435/287.1 |
| 6,472,443 B1 | 10/2002 | Shepodd | 521/63 |
| 6,475,364 B1 | 11/2002 | Dubrow et al. | 204/455 |
| 6,499,499 B2 | 12/2002 | Dantsker et al. | 137/1 |
| 6,518,022 B1 | 2/2003 | Sosnowski et al. | 435/6 |
| 6,551,784 B2 | 4/2003 | Fodor et al. | 435/6 |
| 6,567,163 B1 | 5/2003 | Sandstrom | 356/317 |
| 6,582,660 B1 | 6/2003 | Heller et al. | 422/68.1 |
| 6,613,525 B2 | 9/2003 | Nelson et al. | 435/6 |
| 6,660,480 B2* | 12/2003 | Ramsey et al. | 435/6 |
| 6,664,104 B2 | 12/2003 | Pourahmadi et al. | 435/288.6 |
| 6,726,880 B1 | 4/2004 | Ackley et al. | 422/68.1 |
| 2001/0008212 A1 | 7/2001 | Shepodd et al. | 204/451 |
| 2001/0052976 A1 | 12/2001 | Juncosa et al. | 356/307 |
| 2002/0004204 A1 | 1/2002 | O'Keefe | 435/6 |
| 2002/0028503 A1 | 3/2002 | Ackley et al. | 435/287.2 |
| 2002/0058273 A1* | 5/2002 | Shipwash | 435/6 |
| 2002/0064794 A1 | 5/2002 | Leung et al. | 435/6 |
| 2002/0064800 A1* | 5/2002 | Sando et al. | 435/7.1 |
| 2002/0095073 A1 | 7/2002 | Jacobs et al. | 600/300 |
| 2002/0127565 A1 | 9/2002 | Cunningham et al. | 435/6 |
| 2002/0131899 A1 | 9/2002 | Kovacs | 422/820.1 |
| 2002/0155586 A1 | 10/2002 | Cheng et al. | 435/287.1 |
| 2002/0164628 A1 | 11/2002 | Kurn | 435/6 |
| 2002/0194909 A1 | 12/2002 | Hasselbrink, Jr. et al. | 73/253 |
| 2003/0027354 A1 | 2/2003 | Geli | 436/178 |
| 2003/0048933 A1 | 3/2003 | Brown et al. | 382/128 |
| 2003/0075491 A1 | 4/2003 | Griffiths | 210/198.2 |
| 2003/0082604 A1 | 5/2003 | Swanson et al. | 435/6 |
| 2003/0146100 A1 | 8/2003 | Huang et al. | 204/547 |
| 2003/0151735 A1 | 8/2003 | Blumenfeld et al. | 356/73 |
| 2003/0175947 A1 | 9/2003 | Liu et al. | 435/288.5 |
| 2004/0011650 A1 | 1/2004 | Zenhausern et al. | 204/547 |
| 2004/0052929 A1 | 3/2004 | Kirby et al. | 427/58 |
| 2004/0126279 A1 | 7/2004 | Renzi et al. | 436/180 |
| 2005/0095602 A1* | 5/2005 | West et al. | 435/6 |

FOREIGN PATENT DOCUMENTS

| | | |
|---|---|---|
| EP | 1 385 006 A3 | 1/2004 |
| JP | 2002-286643 | 10/2002 |
| WO | WO 97/12030 A1 | 4/1997 |
| WO | WO 98/49543 A1 | 11/1998 |
| WO | WO 00/09722 A2 | 2/2000 |
| WO | WO 00/09722 A3 | 2/2000 |
| WO | WO 00/30422 A2 | 6/2000 |
| WO | WO 00/79326 A1 | 12/2000 |
| WO | WO 01/44875 A2 | 6/2001 |
| WO | WO 01/44875 A3 | 6/2001 |
| WO | WO 01/45843 A3 | 6/2001 |
| WO | WO 01/53799 A1 | 7/2001 |
| WO | WO 01/69302 A2 | 9/2001 |
| WO | WO 03/004162 A1 | 1/2003 |
| WO | WO 03/036298 A2 | 5/2003 |
| WO | WO 03/036298 A3 | 5/2003 |
| WO | WO 03/064045 * | 8/2003 |

OTHER PUBLICATIONS

U.S. Appl. No. 60/452,985, filed Mar. 6, 2003, Jason West et al.
U.S. Appl. No. 10/795,549, filed Mar. 8, 2004, Jason West et al.
"Gene Logic Chip Patents" Micropatent Search Report created on May 7, 2004.
"MetriGenix" Micropatent Search Report created on May 7, 2004.
"Nanogen (Chips and Devices)" Micropatent Search Report created on May 7, 2004.
"Combimatrix" Micropatent Search Report created on May 7, 2004.
"Zyomyx" Micropatent Search Report created on May 7, 2004.
Ramachandran, N. et al., "Self-Assembling Protein Microarrays," *Science*, Jul. 2, 2004, 305(5680): 86-90 [abstract only].
Alarie, J.P. et al., "Electroosmotically Induced Hydraulic Pumping on Microchips", *Micro Total Analysis Systems*, 2001, 131-132.
Cheek, B.J. et al., "Chemiluminescence Detection for Hybridization Assays on the Flow-Thru Chip, a Three-Dimensional Microchannel Biochip", *Anal Chem*, 2001, 73, 5777-5783.
Doermann, A.H., "Genetic Control of Capsid Length in Bacteriophage T4. Isolation and Preliminary Description of Four New Mutants", *J. Virol*, 1973, 12(2), 374-385.
Gerritsen, V.B. "Baneful Beans", *Protein Spotlight*, 2003, 31, 2 pages.
Kustos, I. et al., "Capillary Electrophoretic Analysis of Wild Type and Mutant *Proteus penneri* Outer Membrane Proteins", *Electrophoresis*, 2000, 21, 3020-3027.
Kustos, I. et al., "Protein Profile Characterization of Bacterial Lysates by Capillary Electrophoresis", *Electrophoresis*, 1998, 19(13), 2317-2323.
Panaro, N.J. et al., "Evaluation of DNA Fragment Sizing and Quantification by the Agilent 2100 Bioanalyzer", *Clinical Chemistry*, 2000, 46(11), 1851-1853.
Schena, M. et al., "Quantitative Monitoring of Gene Expression Patterns with a Complementary DNA Microarray", *Science*, 1995, 270, 467-470.
Svec, F., "Porous Monoliths: The Newest Generation of Stationary Phases for HPLC and Related Methods", *Recent Developments in LC Column Technology*, Jun. 2003, 2-6.
Yu, C. et al., "Monolithic Porous Polymer for On-Chip Solid-Phase Extraction and Preconcentration Prepared by Photoinitiated in Situ Polymerization within a Microfluidic Device", *Anal. Chem.* 2001, 73, 5088-5096.
Yu, C. et al., "Towards Stationary Phases for Chromatography on a Microchip: Molded Porous Polymer Monoliths Prepared in Capillaries by Photoinitiated in situ Polymerization as Separation Media for Electrochromatography", *Electrophoresis*, 2000, 21, 120-127.
"Agilent Technologies Launches AgBio Program with Introduction of Industry's First Microarray to Include Genetic Probes from Two Species", May 15, 2003, 2 pages.
Welcome to MetriGenex. Escape from the Flatland of Microarrays, http://www.metrigenix.com, 30 pages.
"The Scientist, HANAA to Aid Weapons Inspectors", Nov. 28, 2002, http://www.biomedcentral.com/news/20021128/06, 3 pages.
Kreatech-Legal Information, http://www.kreatech.com/legal.html, May 14, 2003, 7 pages.
Kreatech-Science News 2, http://www.kreatech.com/news/news-ssc2.html, May 14, 2003, 10 pages.
Microfluidics-Reversed Chromatography ON for Chem/Bio Warfare Agent Detection, http://www.ca.sandia.gov/microchem/microfluidics/chembiowar.html, 2 pages.
Available Techs: Monolithic Polymers Revolutionize Microfluidic Devices, http://www.lbl.gov/Tech-Transfer/collaboration/techs/lbnl1739.html, May 19, 2003, 2 pages.
"Microarrays: Chipping Away at the Mysteries of Science and Medicine", http://www.ncbi.nlm.nih.gov/About/primer/microarrays.html, May 9, 2003, 11 pages.
Garland, B., M.S., J.D., "Bioethics and Bioterrorism", *The Journal of Philospohy, Science and Law*, Mar. 2002, 2, http://www.psljournal.com/archive/newsedit/bioethics_bioterrorism.cfm, 14 pages.
Sandia seeks Commercialization Partners for Hand-Held Chemical Analysis and Detection System, http://www.sandia.gov/news-center/news-release/2003/mat-chem/chempartners.html, Dec. 17, 2003, 3 pages.
Becker, H. et al., "Polymer Hot Embossing with Silicon Master Structures", *Sensors and Materials*, 1999, 11(5),297-304.
Duffy, D.C. et al., Rapid Prototyping of Microfluidic Systems in Poly(dimethylsiloxane), *Anal Chem.*, 1998, 70, 4974-4984.
Thomas, G.A. et al., "µChemLab™-An Integrated Microanalytical System for Chemical Analysis Using Parallel Gas and Liquid Phase Microseparations", *Proc. SPIE*, 1999, 3713, 66-76.
Chip-Camera Combo Tracks Viruses, *Technology Research News*, Apr. 7, 2004, http://www.technologyreview.com/articles/rnb, 2 pages.

Vandernoot, V. et al., "Incorporation of Sample Preconcentration into the μChemLab™/CB Platform for Enhanced Sensitivity", Oral Disclosure, HPCE 2003, 1 page.

Baba, Y. et al., *Micro Total Analysis Systems: Proceedings of the μTAS Symposium*, Nov. 3-7, 2002, vol. 1 & 2, Kluwer Academic Publishers, Hingham, MA, ISBN: 1-4020-1011-7, (2003).

Houtoff, H. et al., "Platinum-containing Compounds, Methods for their Preparation an Applications Thereof", 1999, Kreatech Diagnostics: Netherlands.

Morbidity and Mortality Weekly Report, Atlanta, Ga., CDC:105.

* cited by examiner

MICROFLUIDIC MICROARRAY SYSTEMS AND METHODS THEREOF

STATEMENT OF GOVERNMENT INTEREST

This invention is made with Government support under contract no. DE-AC04-94AL85000 awarded by the U.S. Department of Energy to Sandia Corporation. The Government has certain rights in the invention.

FIELD OF THE INVENTION

The present invention is related to the field of microfluidic systems and their operation. The present invention is also related to the field of microarrays.

BACKGROUND OF THE INVENTION

Recent advances in miniaturization have led to the development of microfluidic systems that are designed, in part, to perform a multitude of chemical and physical processes on a micro-scale. Typical applications include analytical and medical instrumentation, industrial process control equipment, liquid and gas phase chromatography, and the detection of biological weapons. In this context, there is a need for devices that have fast response times to provide precise control over small flows as well as small volumes of fluid (liquid or gas) in microscale channels. In order to provide these advantages, microarrays are typically integrated on microfluidic chips. The term "microfluidic chip" refers to a system or device having microchannels or microchambers that are generally fabricated on a substrate. The length scale of these microchannels is typically on the micron or submicron scale, i.e., having at least one cross-sectional dimension in the range from about 0.1 micron to about 500 microns.

The development of DNA gene microarray or "microarray" technology capable of detecting thousands of genes in a single experimental test has rapidly advanced and become a widespread application technology. Rapid discrimination of biomolecules such as gene sequences and proteins originating from viruses, bacteria, plants, algae, and eukaryotes such as mammalian cells is useful in a variety of fields, for example health care, food safety, drug testing and bioweapons defense. One drawback of microarray technology in its current format is the long and tedious processing times involved, often requiring up to four days for RNA/DNA sample preparation. Another drawback is that current systems are not designed for quick and portable sensing of biomolecules. In order to tackle these weaknesses in gene microarray analysis there is a need to develop compact systems that combines microfluidics, microarray discrimination, and microarray imaging to efficiently prepare, bind and detect sample target biomolecules.

SUMMARY OF THE INVENTION

In overcoming the problems associated with providing a high throughput microfluidic chip capable of specifically capturing and concentrating nucleic acids for microarray analysis, the present invention provides inter alia, systems including a manifold comprising a plurality of via holes in fluid communication with a plurality of microchannels disposed on a microfluidic chip; the microfluidic chip comprising a microarray; the microfluidic chip capable of transmitting light to the microarray; the microfluidic chip secured to the manifold; an illuminator for providing the light; and a detector in optical communication with the microarray.

Another aspect of the present invention provides methods that include: providing a system including a manifold having a plurality of via holes in fluid communication with a plurality of microchannels disposed on a microfluidic chip; the microfluidic chip including a microarray: the microfluidic chip capable of transmitting light to the microarray; the microfluidic chip secured to the manifold; an illuminator for providing the light; anda detector in optical communication with the microarray; binding at least one biomolecule to the microarray; transmitting light through the microfluidic chip to the microarray; and detecting the at least one bound biomolecule using the detector.

In still other aspects of the present invention there are provided methods, including: fluidically connecting a microfluidic chip to a manifold comprising a plurality of via holes; the via holes being in fluid communication with the microfluidic chip; the microfluid chip including an open channel microarray, sealing the open channel microarray; flowing biomolecules through at least a portion of the via holes to the microfluidic chip; binding the biomolecules to the microarray; transmitting light through the microfluidic chip to the microarray; and detecting bound biomolecules.

Other aspects of the present invention will be apparent to those skilled in the art in view of the detailed description and drawings of the invention as provided herein.

BRIEF DESCRIPTION OF THE DRAWINGS

The foregoing summary, as well as the following detailed description, is further understood when read in conjunction with the appended drawings. For the purpose of illustrating the invention, there is shown in the drawings exemplary embodiments of the invention; however, the invention is not limited to the specific methods, compositions, and devices disclosed. In the drawings.

DETAILED DESCRIPTION OF ILLUSTRATIVE EMBODIMENTS

Figure 1:
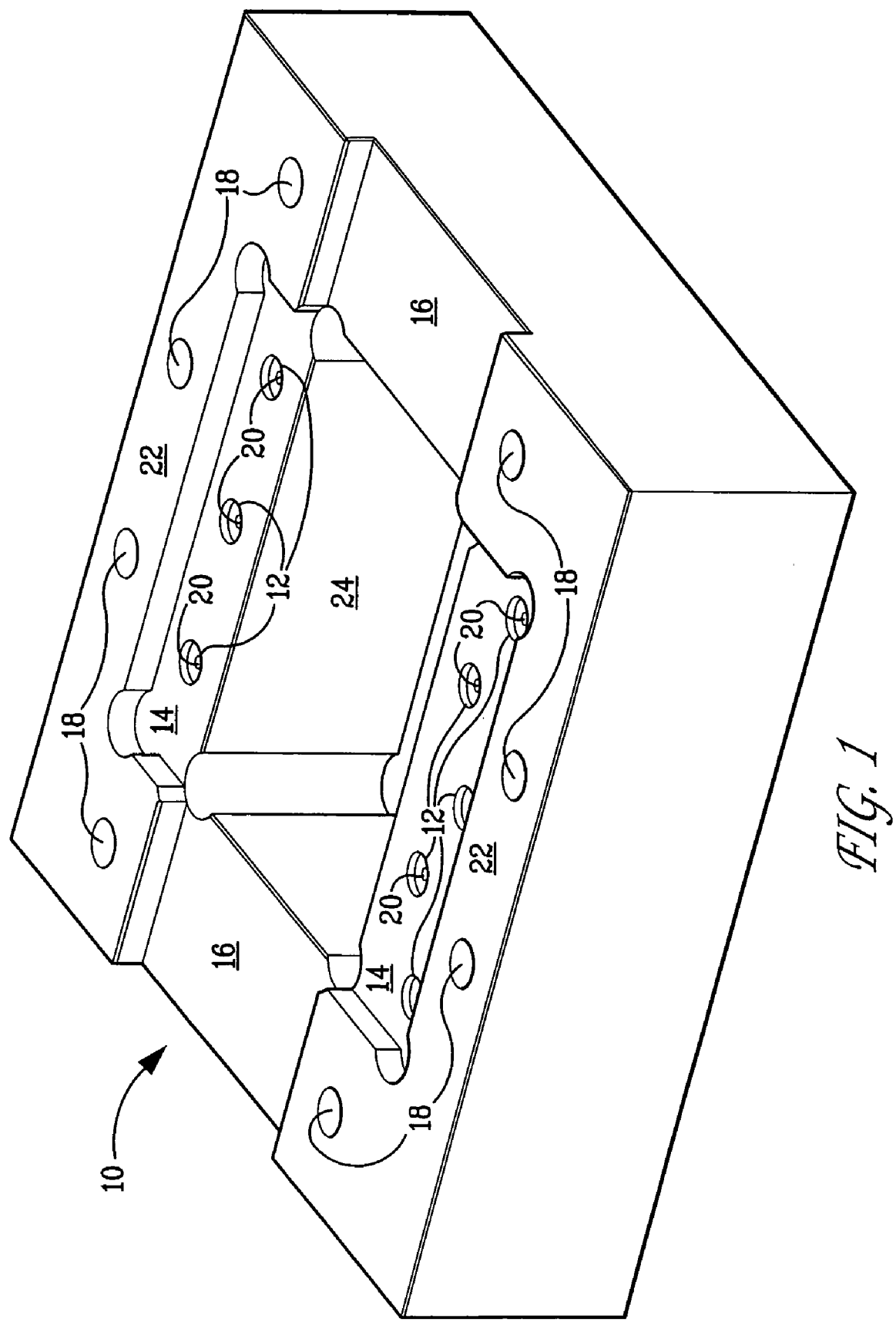
FIG. 1 is a bottom perspective view of an embodiment of a manifold used in the present invention.

The present invention may be understood more readily by reference to the following detailed description of the invention taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When such a range is expressed, another embodiment includes from the one particular value and/or to the other particular value. Similarly, when values are expressed as approximations, by use of the antecedent "about," it will be understood that the particular value forms another embodiment. All ranges are inclusive and combinable.

In one embodiment of the present invention there is provided a system that includes a manifold, a microarray, an illuminator and a detector. The manifold typically includes a plurality of via holes in fluid communication with a plurality of microchannels disposed on a microfluidic chip. Suitable microfluidic chips include a microarray and are capable of transmitting light to the microarray, and are capable of being secured to the manifold. The illuminator typically provides light for ijiuminating the microarray, which is in optical communication with a suitable detector to detect signals emanating from the microarray. Suitable signals include fluorescence from hybridized probe molecules, target molecules, and dyes. Typically the microfluidic chip is secured to the manifold using a backing plate and a compression frame. However, various modes of securing the manifold are possible. Many different types of backing plates can be used; for example, the backing plate can be opaque, translucent, transparent, or any combination thereof. Combinations of two or more backing plates can also be used; for example a transparent backing plate pressed against the microfluidic chip, and an opaque backing plate pressed against the transparent backing plate. Various kinds of backing plates are suitably used. For example, the backing plate can comprise a variety of materials including diamond, quartz, glass, ceramic, silicon or plastic. A suitable backing plate may also comprise two or more materials; for example, an opaque metal frame and a transparent or translucent window interior. In typical embodiments, the system includes microfluidic chips that are optically transparent. Microfluidic chips that are optically transparent help to transmit light to provide an excitation source that excites fluorescent probes residing on the microarray. Transparent microfluidic chips also help to illuminate the various components upon the microfluidic chip.

Suitable manifolds of the present invention typical include at least one fluid port in fluid communication with at least one fluid source. Typically the fluid source includes sample, solvent, buffer, analyte, probe, label, tag, salts, acids, bases, detergents, or any combination thereof. Such fluids are typically transported to, from, or both to and from the microfluidic chip by a suitable fluidic connection, such as an O-ring or seal. Typically there is a plurality of microchannels that comprise open microchannels disposed on a surface of the microfluidic chip. On the microfluidic chip there is also provided a microarray that is in fluid communication with at least one of the microchannels. Thus, fluids are transported to the microarrays by way of the microchannels. Also the microarray typically includes a plurality of biomolecules for testing (e.g., hybridizing) analyte sample molecules. In various embodiments of the present invention, the system includes a manifold and the microfluidic chip wherein the manifold and the microfluidic chip are fluidically sealed with an O-ring at each via hole.

In various embodiments of the present invention, the microfluidic chip is fluidically sealed to a film or substrate. Typically the microarray includes, at least about 100, more typically at least about 1,000, even more typically at least about 5,000, furthermore typically at least about 20,000, and even further typically at least about 50,000 biomolecular spots. In various embodiments of the present invention, at least a portion of the microfluidic chip is fluidically sealed to a substrate. Suitable substrates for sealing the microfluidic chip typically include a film, a transparent window, an opaque window, or any combination thereof. Suitable films comprise a semi-elastic plastic material and are typically compressibly sealed to the microfluidic chip.

In various embodiments of the present invention the microfluidic chip typically includes a surface and features formed in the surface. A suitable substrate or film is fluidically sealed to the chip's surface, features, or both to form structures capable of containing or transporting a fluid. Suitable fluids include sample, solvent, buffer, analyte, probe, label, tag, or any combination thereof. Typically the film fluidically seals features onto the microfluidic chip by way of a compression plug. A suitable amount of pressure for maintaining the fluidic seal can typically maintain a pressure differential of at least about 20 psi (pounds per square inch), more typically at least about 100 psi, and even more typically at least about 300 psi.

Suitable detectors that can be used in various embodiments of the present invention typically include a microscope scanner, photo multiplier tube (PMT), charged coupled device (CCD), or any combination thereof. Preferably, the detector includes a CCD. Typically the CCD is characterized as having a resolution of less than about 50 microns, typically less than about 20 microns, even more typically less than about 10 microns, and even further typically less than about 5 microns. Finer resolution CCDs are also envisioned, such as having a resolution of less than about 2 microns and in certain embodiments even less than a resolution of about 1 micron. The detectors of the present invention suitably include at least about 10,000, more suitably at least about 100,000, even more typically at least about 1,000,000, further typically at least about 5,000,000, and even more typically up to about 10,000, 000 pixels. In certain embodiments the detector is proximately located to the microarray. As used herein the term "proximately" means located near the microarray such that the light detected from the microarray is substantially collected by the detector. Typically the detector is within a few millimeters from the microarray. In preferred embodiment, the detector is aligned parallel to the microarray so that light emanating from the microarray spots is detected by one or more pixels located on the detector.

Suitable microarrays used in various embodiments of the present invention typically include a plurality of biomolecular spots that are disposed on the microarray. Typically the biomolecular spots are disposed in a regular pattern. In alternate embodiments, the biomolecular spots can be randomly arranged on the surface of the microarray. The organization of the spots is not critical as long as the detector detects the signal and location from a spot. The plurality of spots are preferably arranged in a regular array pattern in the microarrays; for example, a typical microarray will include rows and columns of a plurality of bimolecular spots.

The relative orientation of the pixels and the biomolecular spots is not critical, although certain orientations are preferred. The biomolecular spot locations on the microarray is typically registered to at least one of the plurality of pixels on the detector. In certain embodiments, light emanating from at least one of the fluorescent biomolecular spots is detected by at least one pixel on the detector. Accordingly, in various embodiments of the present invention, at least a portion of the pixels are optically coupled to a plurality of biomolecular spots disposed on the microarray. As used herein, the term "optically coupled" refers to the ability of light to be transmitted between two or more points in space. This ability need not require that light is actually transmitted during operation of the invention. More typically, each of the biomolecular spots is optically coupled to at least one pixel. Suitably, in various embodiments, each of the biomolecular spots on the microarray is optically coupled, individually, to at least one pixel. In those embodiments wherein at least a portion of the pixels are optically coupled to a plurality of bimolecular spots disposed on the microarray, it is typical that each of the biomolecular spots is optically coupled to at least two pixels. Among these embodiments, each of the biomolecular spots is optically coupled to an individual group of at least two pixels. Alternatively, each of the pixels can be, independently, optically coupled to one biomolecular spot. More typically each pixel resolves, independently, one biomolecular spot.

Suitably microarrays used in various embodiments include a plurality of biomolecular spots disposed on a portion of a microfluidic chip. Suitable biomolecular spots are typically capable of binding an analyte. Suitable analytes include fluorophores, chromophores, or any combination thereof. Suitable fluorophores and chromophores typically emit a photon that is detected by a suitable detector. Thus, a photon emitted from a fluorophore or chromophore is optically communicated (i.e., transmitted) to a pixel on the detector. Suitably, each of the biomolecular spots on the microarray has a size in the range of from about 60 microns to about 200 microns.

The microarray is typically located proximate to the detector. Typically, each of the biomolecular spots on the microarray is located about 10 microns to about 100 microns from at least one pixel on the detector. The distance between the microarray and the detector is suitably kept below about 200 microns so that photons emitted from a fluorophore or chromophore of a biomolecular spot are optically communicated to at least one pixel on the detector.

The optical communication of photons emitted from the surface of the microarray to the detector can be accomplished using an optical coupling situated between the microfluidic chip and the detector. Suitable optical couplings include an optical waveguide, a lens, an optical fiber bundle, a transparent (e.g., glass or plastic) rod, a fiber plate, an aperture, or any combination thereof. In certain preferred embodiments of the present invention, the optional optical coupling includes an optical fiber bundle including a plurality of optical fibers, each of the fibers having a diameter in the range of from about 1 micron to about 10 microns. In embodiments comprising optical fiber couplings, typically one end of each fiber is optically coupled to at least one pixel on the detector. Certain preferred optical couplings include optical fibers that are oriented to provide a magnified or reduced image of the microarray to the detector.

Suitable illuminators are typically adjacently secured to the microfluidic chip to provide a source of excitation illumination to the analyte molecules situated on the microarray. Suitable illuminators are typically secured to at least one edge of a transparent or translucent microfluidic chip. The illuminator is not necessarily fixed to the microfluidic chip; howeverjn preferred embodiments, the illuminator is secured to the edge of the microfluidic chip using a suitable holder such as a compression fitting, holding bar, or screw. Suitable illuminators typically include a waveguide to provide light to the microarray. Illuminators that are secured to an edge of the microfluidic chip typically provide light into the edge of the microfluidic chip. Suitable illuminators typically include a light source and a waveguide that includes a fiber bundle. The fiber bundle is capable of directing light from an external light source to the microarray. Accordingly, illuminators that include a waveguide further include an illumination source. Suitable illumination sources typically include a light emitting diode ("LED"), an incandescent light source, a fluorescent light source, an electroluminescent light source, a plasma light source, a laser or any combination thereof. In certain preferred embodiments of the present invention, the illuminator includes an LED. Suitable LEDs are capable of emitting a variety of light wavelengths (i.e., different colors, for example, red, blue, yellow, green, or white). A variety of two or more light sources can be combined to provide further wavelength distribution, (i.e., mixing colors). For example, light sources can be combined using a split fiber optic bundle connected to two LEDs at the split ends. Typically the illuminator includes at least one LED coupled to at least one waveguide. In other embodiments, the system of the present invention further includes at lease two illuminators capable of emitting the same or different wavelengths of light. In certain embodiments having more than one illuminator it is typical that each of the illuminators are individually coupled to a waveguide. In other embodiments each of the illuminators may emit the same or different wavelengths of light. Suitably, in embodiments including more than one illuminator it is even more preferred that the illuminators include a LED light source.

In certain embodiments of the present invention, the systems further include a temperature controller for controlling the temperature of the microfluidic chip. Suitable temperature controllers typically include a thermoelectric cooler. The temperature controller may be in direct or indirect thermal physical contact with the microfluidic chip or it may be in radiative thermal contact with the microfluidic chip. As used herein, "indirect contact" means that at least one other material is situated between the temperature controller and the microfluidic chip, e.g., a plate or film. Preferably, the temperature controller contacts the microfluidic chip so that heat from the thermoelectric cooler flows into the microfluidic chip directly through physical contact (heating mode). Alternatively, heat from the microfluidic chip flows into the thermo/electro cooler (cooling mode). Accordingly, a suitable temperature controller is capable of heating and cooling the microfluidic chip. Most typically the controller is capable of controlling the temperature of the microfluidic chip in the range of from about 40° C. to about 120° C. Controlling the temperature of the microarray is typically useful during hybridization and annealing of nucleic acids. The temperature controller can also be used for PCR cycling, preparation reactions on the microfluidic chip, and heating to elute mRNA for preparing the microarray to accept sample genetic material, and any combination thereof.

In various embodiments in the present invention, there are also provided methods that include providing a system of the present invention, binding at least one biomolecule to a microarray, transmitting light through a microfluidic chip to the microarray, and detecting at least one bound biomolecule using a detector. In suitable methods of the present invention, the system includes a manifold that includes a plurality of via holes in fluidic communication with a plurality of microchannels disposed on a microfluidic chip, the microfluidic chip including a microarray, the microfluidic chip capable of transmitting light to the microarray, and the microfluidic chip being secured to the manifold. Systems used in these methods suitably include an illuminator for providing the light and also include a detector in optical communication with the microarray to detect light emanating from the various spot positions on the microarray. Any type of biomolecular binding interaction to the microarray is envisioned. Suitable binding of biomolecules to the microarray typically includes at least one of: hybridization of nucleic acids, interactions between two or more proteins, interactions between at least one nucleic acid and at least one protein, and any combination thereof. Suitably, hybridization of nucleic acids is typically achieved by binding nucleic acids to the microarray spots, flowing analyte nucleic acids to the microarray, and annealing analyte nucleic acids to one or more complementary nucleic acid spots on the microarray. Suitably, the analyte biomolecules include one or more of a label, a tag, a dye, a biomarker, or any combination thereof, bound to the biomolecule. Suitably, the label, tag, dye, or biomarker includes a fluorescent tag that is typically excited by light emanating from the illuminator. Thus, the biomolecule that fluoresces at a particular position when bound to the microarray provides information to the detector. This microarray detected position information is subsequently analyzed by a data processor to indicate the identification of the detected biomolecule. Further details concerning the preparation and use of microarrays to detect biomolecules are provided in U.S. patent application Ser. No. 10/701,097, "Microfluidic Integrated Microarrays for Biological Detection", filed Nov. 4, 2003, the entirety of which is incorporated by reference herein.

In other embodiments of the present invention, there are provided methods that include fluidically connecting a microfluidic chip to a manifold. Suitable manifolds include a plurality of via holes, and preferably include via holes that are in fluidic communication with the microfluidic chip. The microfluidic chip preferably includes an open channel microarray capable of receiving nucleic acids that are fluidically transported from the manifold and through the vias. In these various methods, open channel microarrays are sealed and sample molecules (i.e., analyte) flow through at least a portion of the via holes to the microfluidic chip. The biomolecules are bound to the microarray, and light is transmitted through the microfluidic chip to the microarray. Detection of the bound molecules typically ensues using a suitable detector capable of detecting light emitted from fluorescing molecules. Flowing the biomolecules through at least a portion of the via holes to the microfluidic chip is suitably obtained by flowing the biomolecules under the influence of a pressure differential, an electrical potential, an osmotic potential, or any combination thereof. Typically the binding includes hybridization of nucleic acids, interactions between two or more proteins, interactions between at least one nucleic acid and at least one protein, or any combination thereof. Typically the biomolecule includes a label, a tag, a die, a biomarker, or any combination thereof, covalently bound to the biomolecule.

FIG. 1 illustrates a manifold (10) used in the present invention. The manifold (10) has a plurality of manifold fluidic chip interfacing via holes (20) each having an O-ring recess (12). Vias (not shown) on the microfluidic chip (not shown) are fluidically sealed to the via holes (20) through suitable O-rings (not shown) placed in the O-ring recesses (12). A microfluidic chip can be physically secured in the manifold (10) by placement in fluidic chip recesses (14) that secure opposite edges of the microfluidic chip. Alternative configurations of recesses are envisioned wherein more than two edges of the microfluidic chip can be secured. Other ways of securing the chip to the manifold are also envisioned; for example, one edge can be secured by a recess, and another edge can be secured by an adhesive clamp or seal. Although it is preferred that the fluidic chip recesses are positioned to secure opposing edges of a suitable microfluidic chip, in other embodiments it is envisioned that at least one fluidic chip recess can be adjacent to at least one other fluidic chip recess. Also, a manifold having one chip recess is envisioned. A suitable manifold having one fluidic chip recess can have any type of shape, such as a circle, cone, square, triangle, rectangle, or any other type of polygon, or a combination thereof.

The illuminator recesses (16) illustrated in FIG. 1 are depicted as channels for holding a suitable illuminator (not shown) in the manifold. Accordingly, the preferred manifold as shown has fluidic chip recesses (14) and illuminator recesses (16) to secure, separately or simultaneously, a microfluidic chip and one or more illuminators. Preferably, at least one illuminator edge is capable of optically transmitting light into at least one microfluidic edge. Although it is preferred that the illuminator edge contacts a microfluidic edge, physical contact between the edges is not necessary to transmit at least a portion of the light from the illuminator into, or onto, the microfluidic chip. As shown in FIG. 1, the recesses (14) and (16) provide one microfluidic chip having two edges that can contact two illuminators. Other variations of the illuminator and microfluidic chip recess combinations are envisioned. Although suitable microfluidic chips are preferably square or rectangular in shape, the microfluidic chips may have any type of shape, such as a circle, cone, square, triangle, rectangle, or any other type of polygon or combination thereof.

FIG. 1 further illustrates a chip access port (24) that resembles a rectangular channel positioned beneath the placement of the microfluidic chip recesses. The chip access port (24) provides access to the chip for preparing a suitable microarray onto a chip that is mounted into the manifold. The chip access port (24) can also provide for optical communication of detection of the microarray to a suitable detector (not shown) positioned in optical communication with the chip access port (24). The chip access port (24) suitably may contain one or more optical communication waveguides; for example, a fiber bundle (not shown) in which light transmitted from the microarray is received by the detector positioned proximate to the manifold (10). This bottom view of a manifold (10) further provides a plurality of mounting screw holes (18). The mounting screw holes suitably are used for clamping the microfluidic chip between the manifold and an opposing clamping surface. A suitable opposing clamping surface includes, for example, at least one backing plate that is transparent, translucent, opaque, or any combination thereof, as described herein. FIG. 1 also shows that the bottom surface of the manifold (10) is raised respective to the recesses (14) and (16) for the microfluidic chip and the one or more illuminators, respectively.

Figure 2:
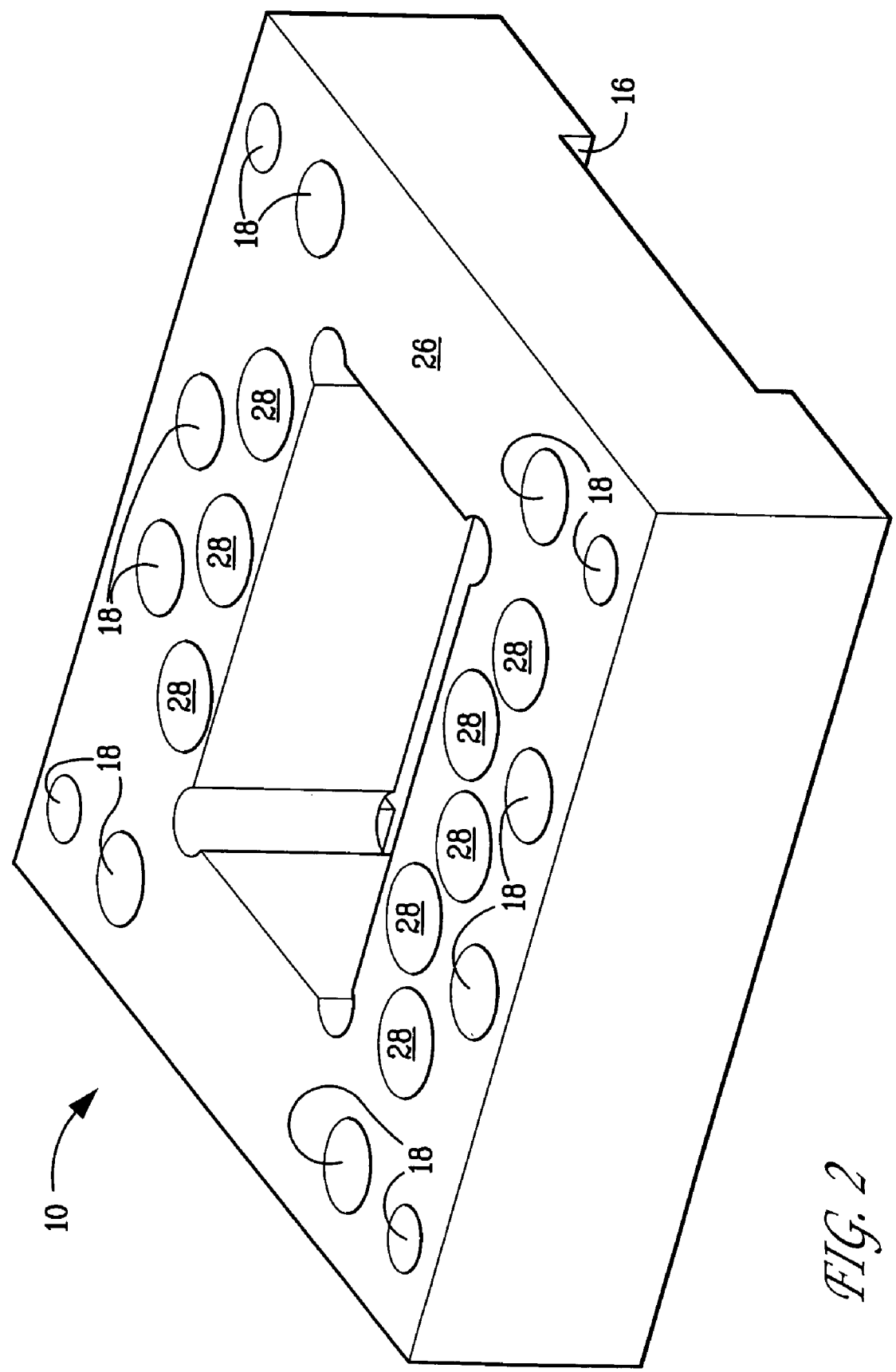
FIG. 2 is a top perspective view of an embodiment of a manifold used in the present invention.

FIG. 2 illustrates a top surface of the manifold described in FIG. 1. The top surface (26) of the manifold (10) is illustrated with the plurality of mounting screw holes (18) and illuminator recess (16). A plurality of manifold fluidic ports (28) penetrating the manifold (10) are appropriately indicated using dashed lines. Eight fluidic ports (28) are shown in FIG. 2. The plurality of manifold fluidic ports (28) fluidically connect sources of fluids for example samples, analytes, and buffers into and out of the microfluidic chip that is mounted to the manifold. For example, an analyte solution comprising of a buffer, an analyte and water that is contained in a sample volume can be connected fluidically to the manifold through a suitable capillary (not shown). Fluids are typically pumped under pressure through at least one of the manifold fluidic ports (28) and through the corresponding via hole (shown as dashed lines). At least one other fluidic port is typically connected to a waste line to remove excess fluid from the microfluidic chip. A plurality of manifold fluidic ports are provided for providing a plurality of fluids and also for receiving waste solutions from various portions of the microfluidic chip.

Figure 3A:
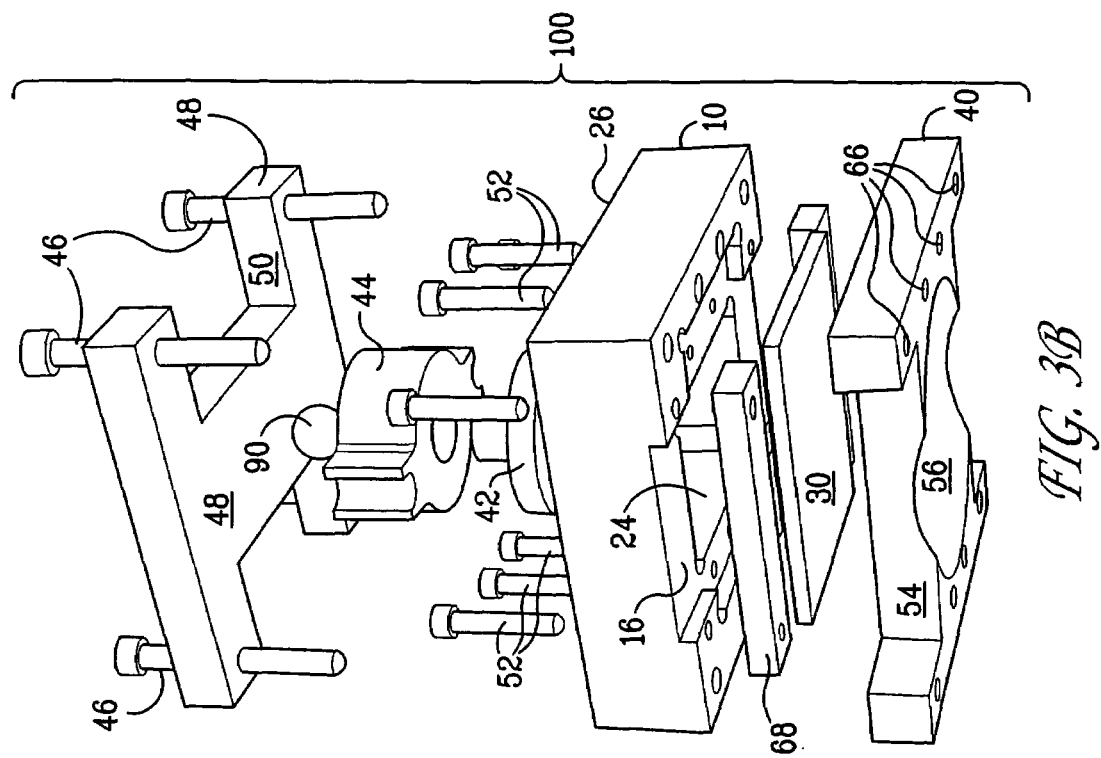
FIG. 3 is an exploded perspective view of a portion of an embodiment of a system of the present invention (illuminator and detector not shown).
Figure 3B:
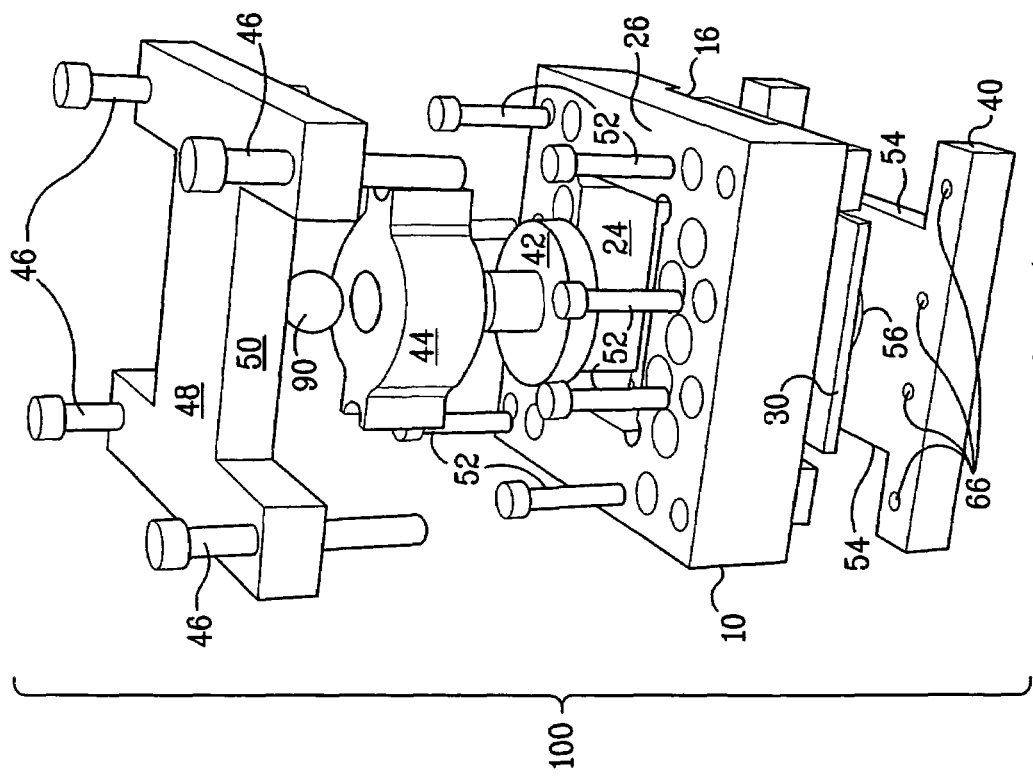

FIG. 3 illustrates an exploded perspective view of a portion of a system of the present invention in which an illuminator and a detector are not shown. This embodiment shows a manifold (10), a microfluidic chip (30), and a compression backing plate (40). The manifold and the compression backing plate are fixedly secured using screws (52) to hold the microfluidic chip (30) on the manifold (10) between the fluidic chip recesses (not shown). The compression backing plate (40) is shown comprising a plurality of mounting holes (66) for receiving screws (52) and (46). The compression backing plate also shows a chip access port (56). This chip access port is used for receiving optical information from the microarray situated on the microfluidic chip. This chip access port can also be used for other functions that need to be performed on the microfluidic chip; for example, spotting, filling, and sealing the chip. The compression backing plate (40) is further shown having two illuminator notches (54) for positioning a suitable illuminator (not shown). The space provided for the illuminator notches on the compression backing plate is typically larger than the illuminator recesses (16) on the manifold (10). Although the illuminator can be held in the illuminator recesses (16) using a variety of methods, for example, a clip or screw, preferably there is provided a bar (not shown) for securing the illuminator to the manifold (10) using mounting screws affixed to the manifold. Methods for mounting the illuminator is further described below.

The system (100) in FIG. 3 further illustrates a manifold having a top surface (26) of the manifold oriented upwards. The manifold (10) also is shown with chip access port (24) and a compression plug (42) that fits within the chip access port (24). This compression plug (42) is positioned using a compression plug positioner (44) that holds the compression plug (42) against a suitable film or substrate placed on the chip for sealing the microfluidic structures (not shown). A compression frame (48) holds the compression plug positioner (40) against the compression plug (42) using screws (46) that are screwed through the manifold and into the compression backing plate (44). The compression plug (42) presses against the film or substrate (not shown) and the microfluidic chip. The compression frame (48) is further shown having fluidic port access notches (50). The fluidic port access notches (50) permit placement of suitable fluid transfer tubing (not shown) into the plurality of the manifold fluidic ports (28). When assembled together, the system (100) provides a fluidically sealed microfluidic chip that is capable of receiving fluids, transferring fluids to and from a microfluidic chip, exiting fluids, and providing an access port for visualizing a microarray situated on the microfluidic chip. Use of this assembly provides ease of manipulation of various components as shown herein. The microfluidic chip (30) can be spotted when the system (100) is assembled or unassembled. In further embodiments shown below, an illuminator, a detector and an optional temperature controller are further assembled with the system.

Figure 4:
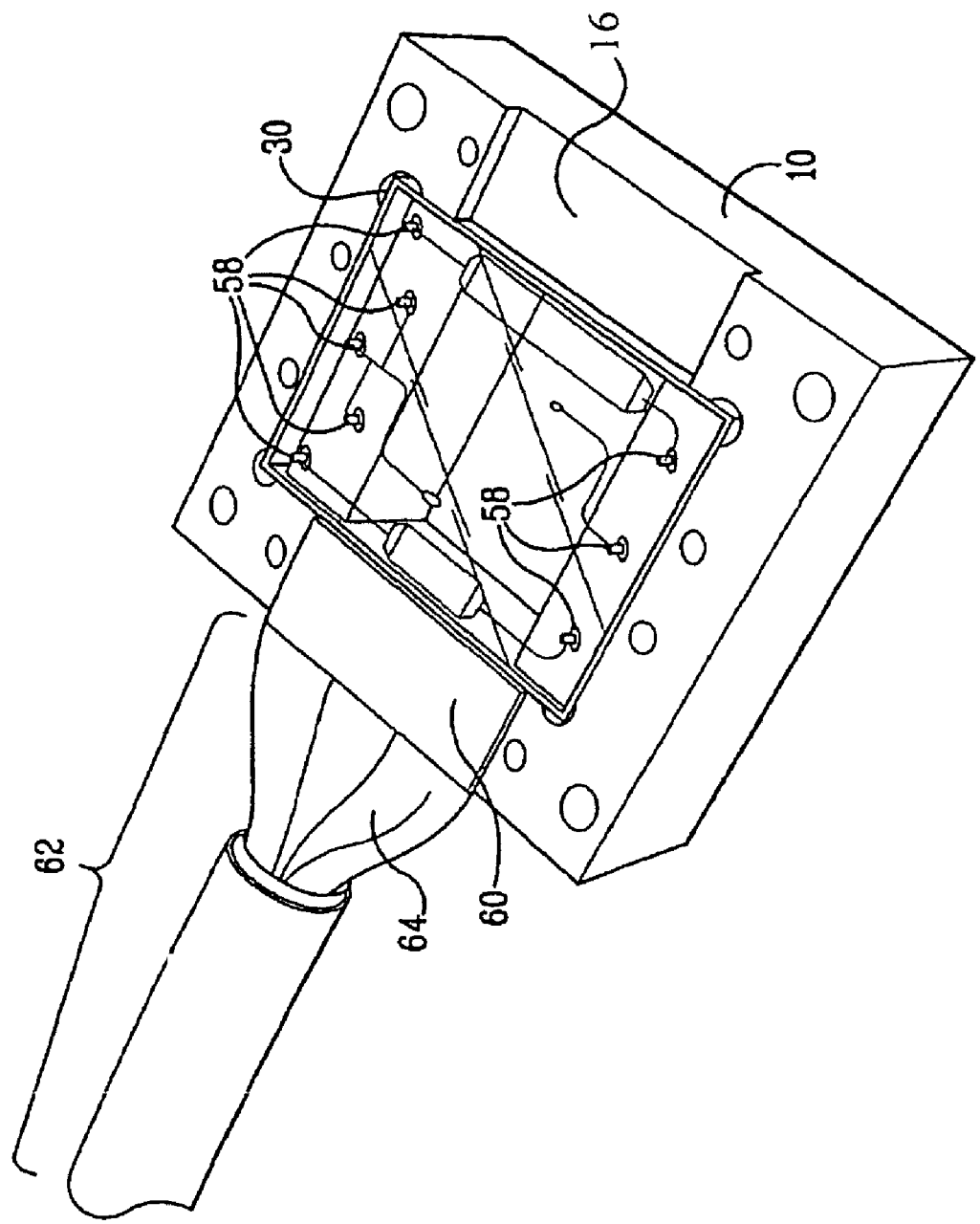
FIG. 4 is a schematic perspective view of a portion of an embodiment of a system of the present invention (detector and compression frame not shown).
Figure 5:
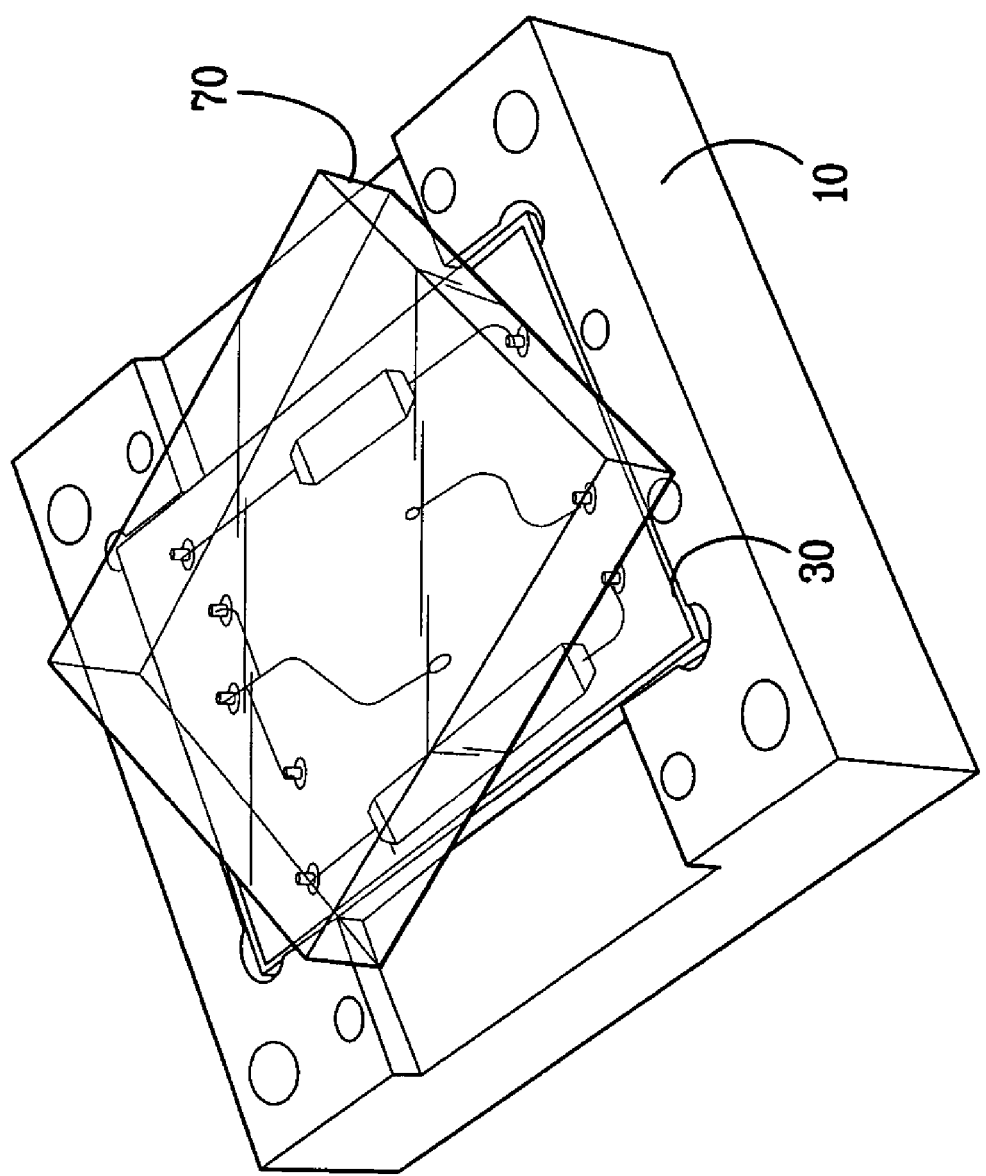
FIG. 5 is a schematic view of an embodiment of a manifold, microfluidic chip and a transparent backing plate (the transparent backing plate is shown unaligned with the microfluidic chip).

FIG. 4 illustrates a portion of a system of the present invention. In this figure a suitable detector and compression frame are not shown. This figure illustrates the manifold (10) on which is placed a microfluidic chip (30). The microfluidic chip includes a plurality of via holes (58) that are adjacent to the plurality of the manifold chip interfacing via holes (20). Shown proximate to the left edge of the microfluidic chip in this figure is an illuminator (60), which can be adjacent to or proximate to the edge of the chip. As used herein, the term "proximate" means located close enough to affect a functional relationship between the two components. In this case, the illuminator functions by supplying light into the edge of the microfluidic chip. The illuminator (60), which resides in one of the two illuminator recesses (16), includes an optical fiber bundle (62) that comprises a plurality of individual optical fibers (64). The optical fibers (64) are held in a rectangular shape to fit within the illuminator recess of the manifold. Other shapes are envisioned such as circles, squares, triangles, and any other geometry in which light can be transmitted into or onto the microfluidic chip. Light can be transmitted to the microarray in any type of manner that is capable of illuminating the microarray. Suitable microarrays receive the light, fluorescent probes bound to the microarray are excited, excitation light is emitted by the probes, and the emitted light is detected by a suitable detector FIG. 5 illustrates a manifold, a microfluidic chip and a transparent backing plate. For illustration purposes, the transparent backing plate (70) is shown situated unaligned atop the manifold (10) and the microfluidic chip (30). The thickness of the transparent backing plate in this embodiment is selected to compress against the microfluidic chip using the compression backing plate (not shown). Suitable transparent backing plates are typically thicker than the microfluidic chip (30). In addition, suitable transparent backing plates are capable of receiving light from a suitable illuminator and transmitting the received light to the microarray. Suitable backing plates for optically communicating light are typically transparent or translucent. Typical transparent backing plates can be made from any transparent material such as glass, plastic, ceramic, or any combination thereof. Although the transparent backing plate preferably is optically clear, suitable transparent backing plates can also be used that scatter some of the excitation or emitted light. In certain embodiments, the transparent backing plate may be somewhat translucent as long as the detector is capable of resolving the point of origin of the emitted light from the microarray. Emission light from the microarray is transmitted through the transparent backing plate and received by a suitable detector (not shown). In alternate embodiments, the detector can be placed beneath the microfluidic chip opposite to the side of the transparent backing plate. Various orientations of the transparent backing plate and detector are envisioned and can be practiced by one skilled in the art in view of the disclosure provided herein.

Figure 6:
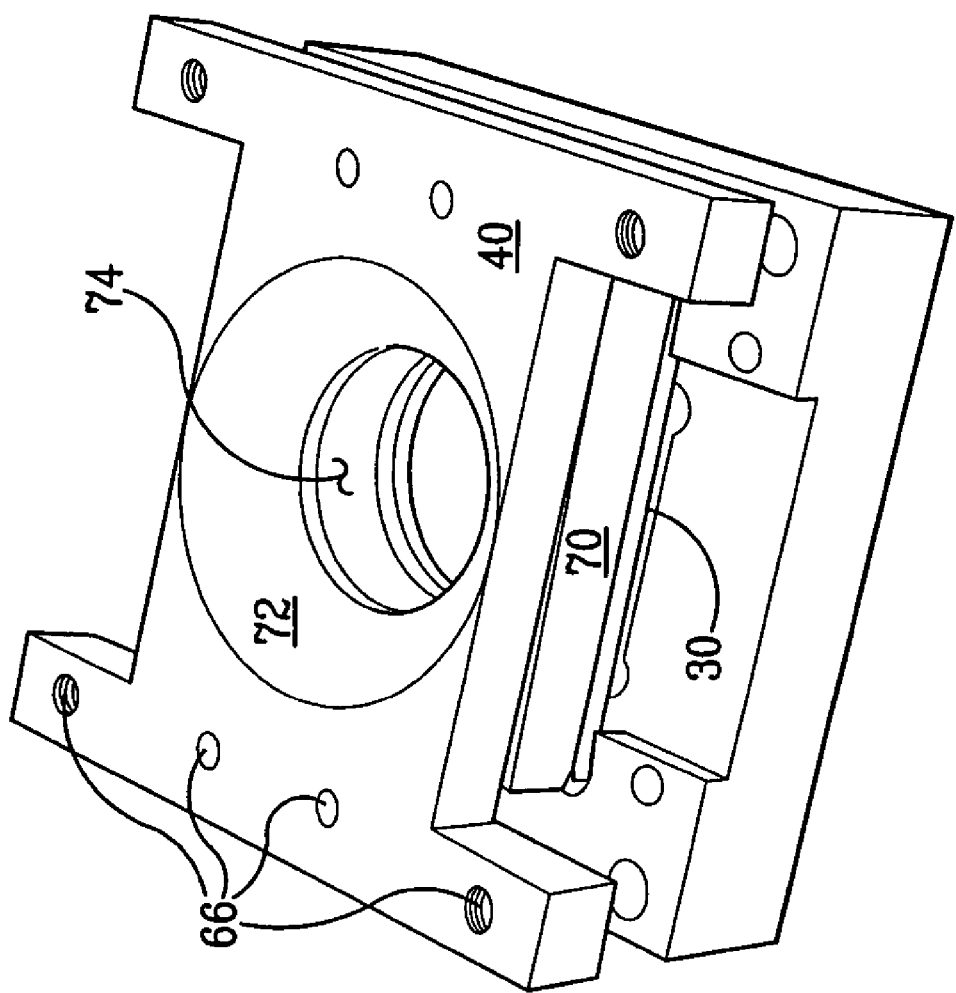
FIG. 6 is a schematic perspective view of an assembled portion of an embodiment of a system of the present invention (illuminator and detector not shown).

FIG. 6 illustrates a partially assembled portion of a system of the present invention (illuminator and detector not shown). This figure shows a compression backing plate (40) comprising a plurality of mounting holes (66). Also provided on the compression backing plate is a beveled channel (72) that provides a viewing port (74) for viewing the microfluidic chip (30) located beneath the transparent backing plate (70). The viewing port (74) is situated in the center of the beveled channel (72), although other positions of the viewing port are envisioned. The beveled channel (72) suitably can hold an optical fiber bundle or other waveguide for transmitting light from the microarray through the transparent backing plate (70) to a suitable detector (not shown). This assembly of compression backing plate, transparent backing plate, microarray, and manifold (10) is held together by mounting screws (not shown). In related embodiments the optional beveled channel (72) can be replaced with a non- beveled channel. A suitable detector can be placed flush at the top surface of the compression backing plate (40) for receiving optical signals transmitted through the viewing port (74).

Figure 7:
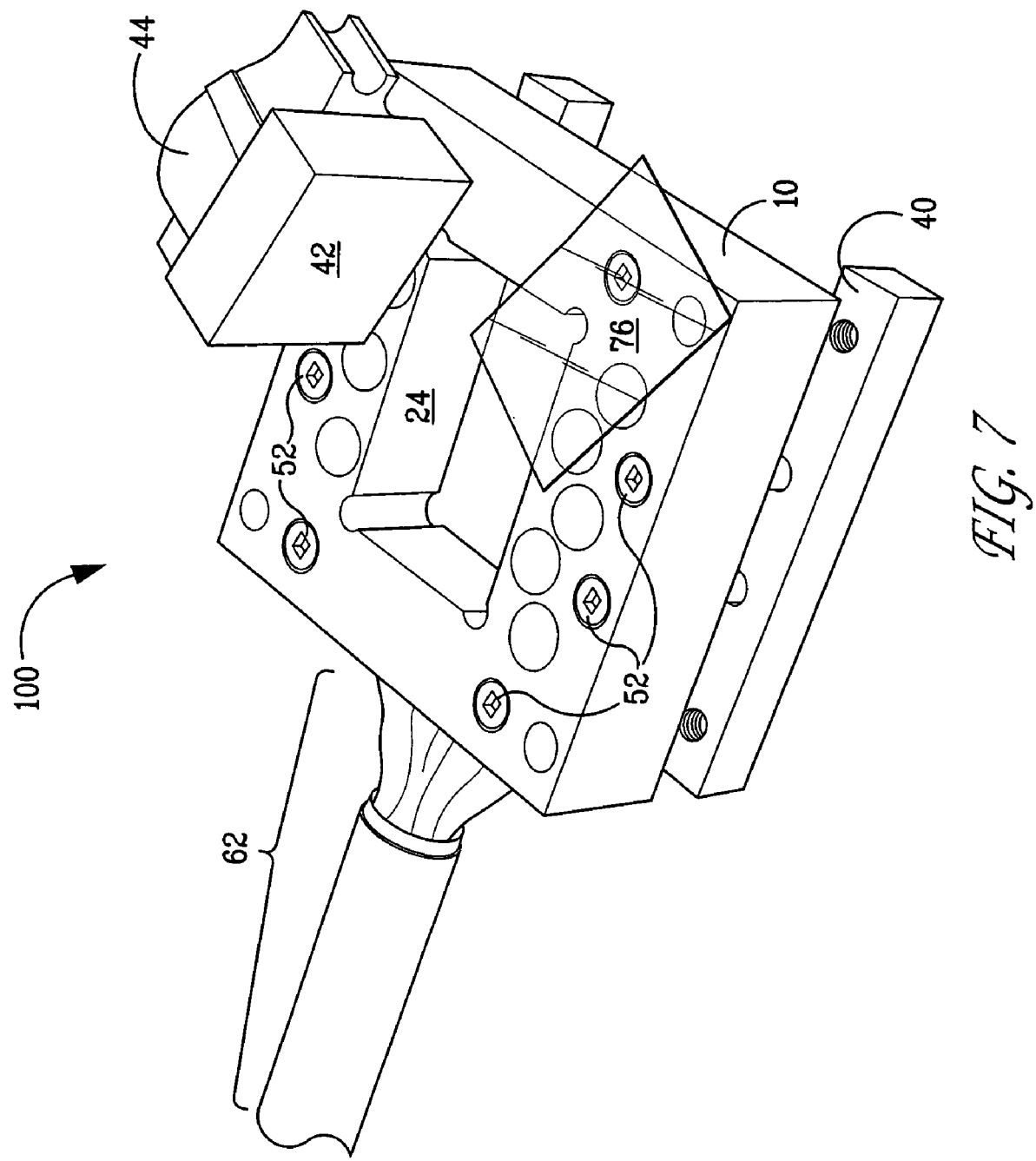
FIG. 7 is a perspective view of a portion of an embodiment of a system of the present invention in which a compression plug, a compression plug positioner and a film are removed (illuminator and detector not shown).

FIG. 7 illustrates a portion of a system (100) in which a compression plug (42), a compression plug positioner (44), and a film (76) are removed. This embodiment further shows mounting screws (52) that hold the manifold (10) to the compression backing plate (40). The film (76) and the plug (42), and plug position (44) are removed to illustrate the approximate sizes of these components relative to the manifold (10). The manifold (10) is shown comprising chip access port (24). The film (76) is placed on top of the fluidic chip through port (24) and is held in place using plug (42) and plug positioner (44). A suitable compression frame (48), as shown in FIG. 3, holds the plug positioner and plug securely against the film (76) and the microfluidic chip (not shown). The optical fiber bundle (62) is shown attached through one of the illuminator recesses (not shown).

Figure 8:
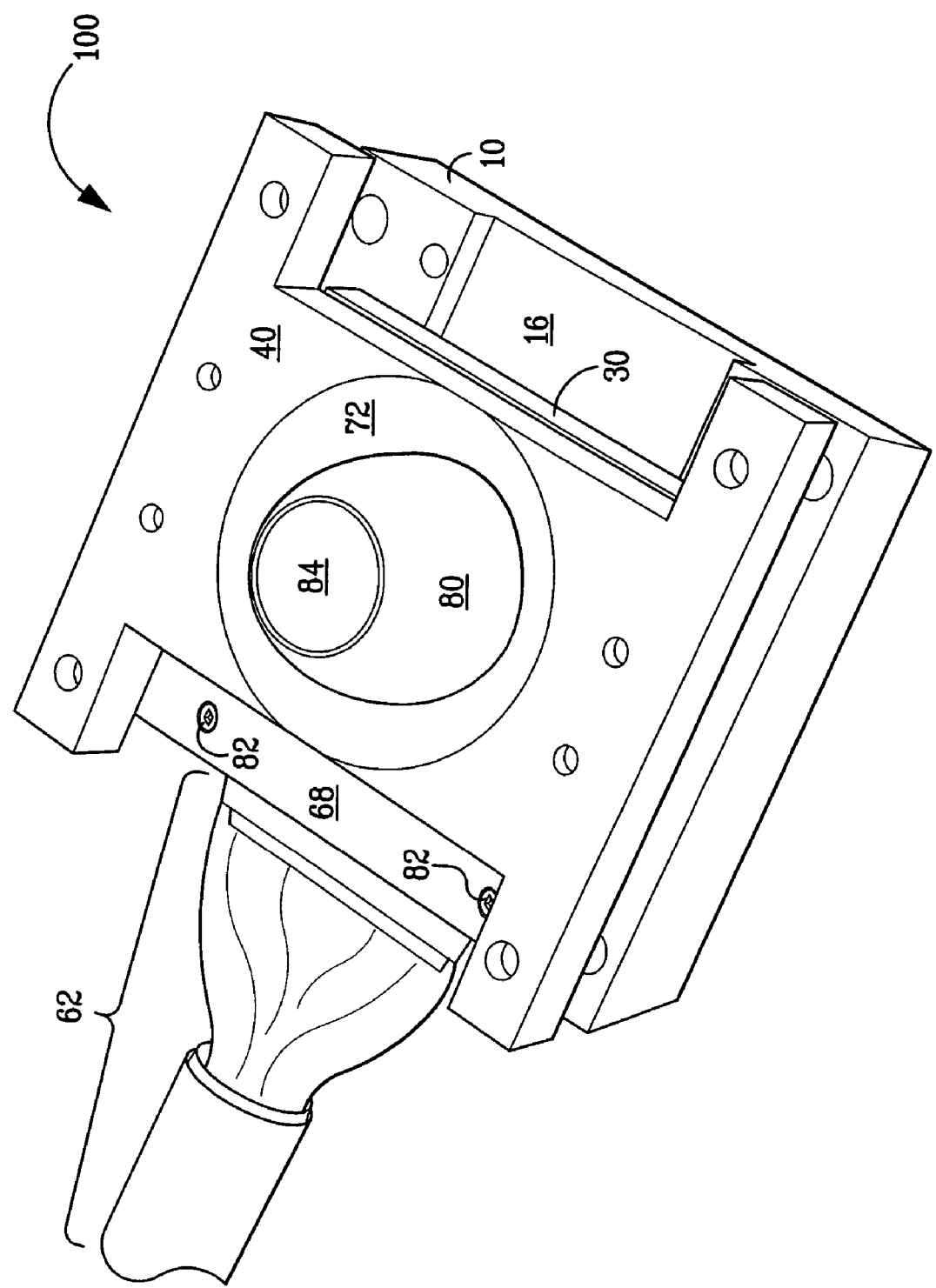
FIG. 8 is a schematic perspective view of an assembled portion of an embodiment of a system of the present invention that shows placement of an optical fiber bundle placed in a beveled channel of a compression backing plate (illuminator and detector not shown).

FIG. 8 illustrates an assembled portion of a system (100) that shows an optical fiber bundle (80) placed in beveled channel (72) of a compression backing plate (40). In this figure, the detector is not shown. The optical fiber bundle (80) is shown including an image reducing surface (84). The larger surface of the optical fiber bundle (80) is shown situated in the beveled channel (72) adjacent to the microfluidic chip (30). The optical fiber bundle receives light from a microarray or other object on the microfluidic chip and transmits the light through the bundle and out of surface (84). In this configuration a larger area on the microarray is reduced to a smaller area (84) using the optical fiber bundle for reducing the image. A suitable detector is placed approximate to surface (84) to receive the reduced image. In this embodiment detectors smaller in area than the area of the microarray are suitably used. In alternate embodiments, for example, the optical fiber bundle (80) can be oppositely placed in which the image reducing surface (84) is placed adjacent to the microfluidic chip (30) and a magnified image is presented to a suitable detector. In various configurations a combination of waveguides and fiber optic bundles are envisioned for transmitting light from more than two areas on a microfluidic chip to one or more detectors that are in optical communication with the microfluidic chip. FIG. 8 also shows an illuminator holding bar (88) that includes mounting screws (82) for holding and positioning the illuminator (06) with respect to the assembly of the microfluidic chip (30) and manifold (10). The illuminator holding bar (68) holds the rectangular portion of the illuminator (60) adjacent to the manifold and microfluidic chip using screws (82). This orientation of the apparatus helps to achieve quick-changing and assembly of the system (100).

Figure 9:
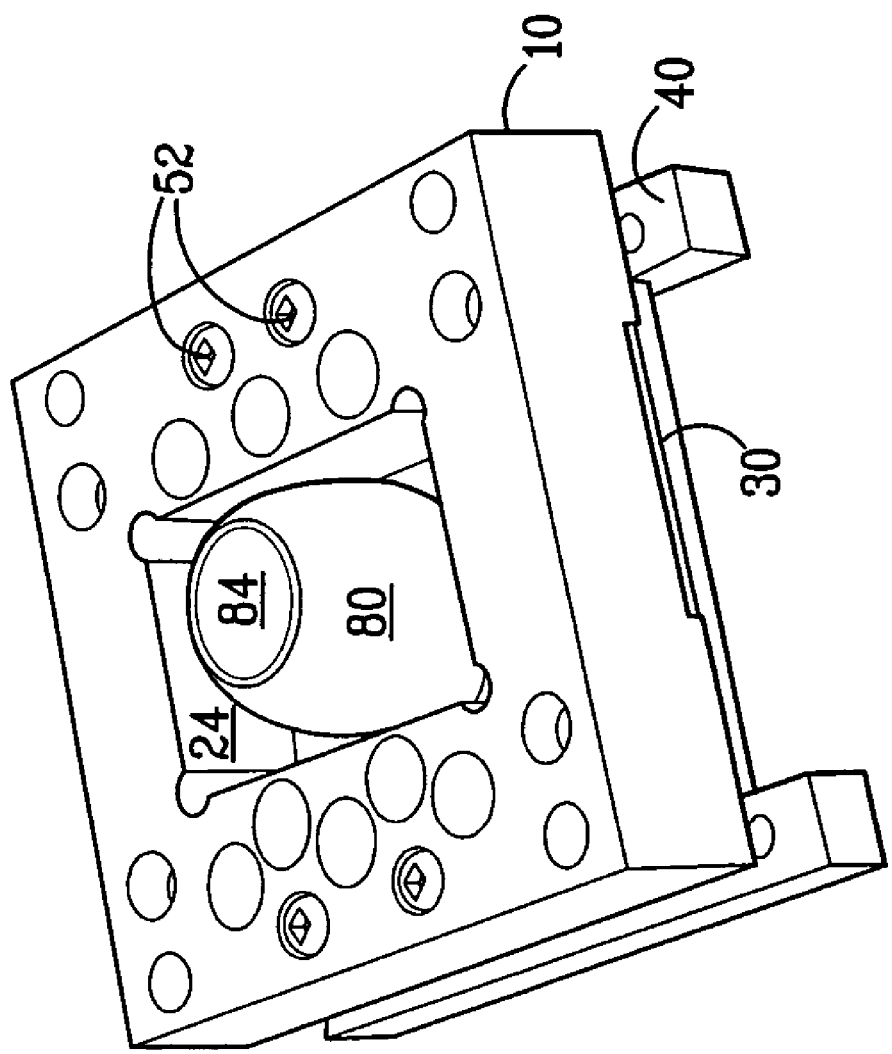
FIG. 9 is a schematic perspective view of an assembled portion of an embodiment of a system of the present invention that shows placement of an optical fiber bundle placed in a chip access port of a manifold (illuminator and detector not shown).

FIG. 9 provides an alternate embodiment of the system (100) wherein the optical fiber bundle (80) is placed within the microfluidic chip access port (24). In this embodiment, the image reducing surface (84) of the optic fiber bundle (80) is oriented to be adjacent to, or proximate to, a suitable detector (not shown). In this embodiment the optic fiber bundle (80) can also function as a compression plug for compressing a film or substrate between the optic fiber bundle and the microfluidic chip. The film or substrate that is compressed to the microfluidic chip suitably fluidically seals structures on the microfluidic chip (30). The film (not shown) can be made from any of suitable substrate including a glass or plastic material. Screws (52) affix the manifold (10) to the compression backing plate (40).

Figure 10:
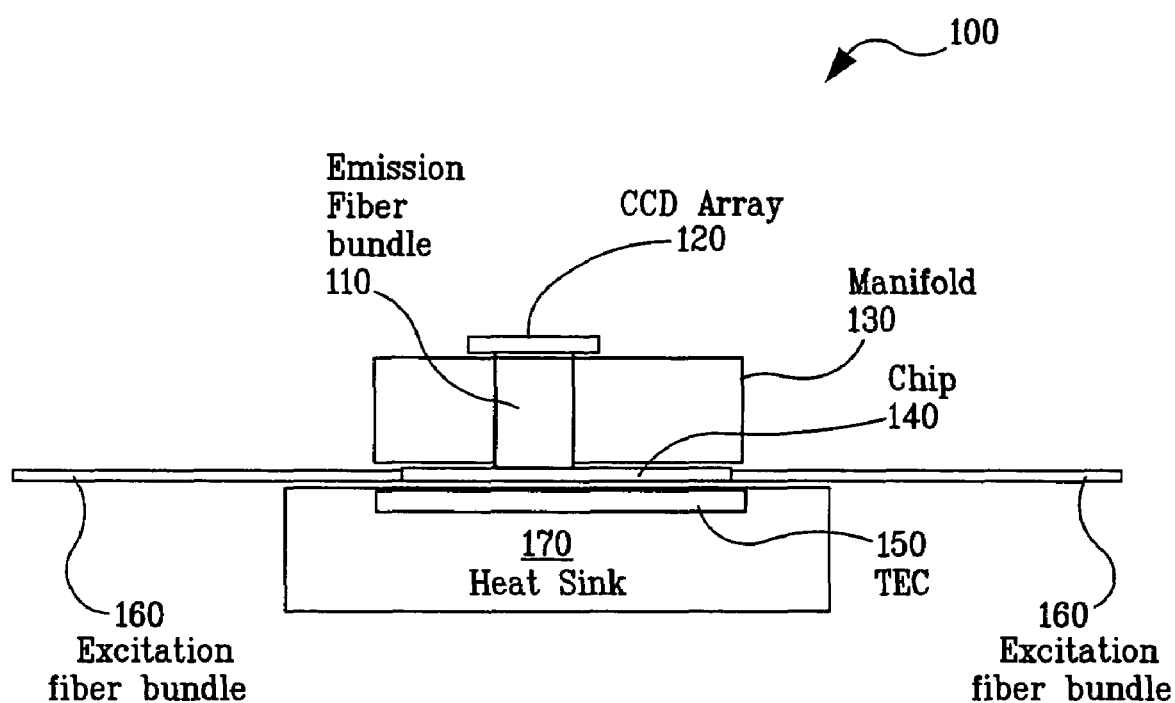
FIG. 10 is a schematic of one embodiment of a system of the present invention.

FIG. 10 illustrates a system (100) of the present invention. This figure shows a microfluidic chip (140) placed between a manifold (130) and a thermoelectric cooler (150). The thermoelectric cooler (150) ("TEC") is further situated above a heat sink (170). In this embodiment the thermoelectric cooler controls the temperature of the microfluidic chip. Temperature control of the microfluidic chip helps to enable hybridization and annealing of nucleic acids on a microarray placed on the chip. Placement of a CCD detector (120) is shown above an emission fiber bundle (110), which transmits light from the microarray on the chip to the CCD detector. Excitation is provided by two excitation fiber bundles (160) that are schematically shown adjacent to opposite edges of the microfluidic chip (140). Various embodiments of the system shown herein are also envisioned. For example, one or more excitation fiber bundles (160) can be present. The emission fiber bundle (110) can be replaced with a different type of waveguide, for example, a glass or plastic waveguide. In certain embodiments, the emission fiber bundle need not be present. In alternate embodiments, the CCD detector may be replaced with another suitable detector. The orientation of the heat sink in the thermoelectric cooler can be changed such that the thermoelectric cooler is placed on top of the manifold and the chip is placed between the manifold and the thermoelectric cooler. The heat sink is optional and can be replaced by other material forms within the system of the present invention. For example, the thermoelectric cooler can be placed not on a heat sink but on a mounting bracket or suitable compression backing plate.

EXAMPLES

A system as described herein and illustrated in FIGS. 1-10 was fabricated to establish fluidic connection between microfluidic microarray chips and fluidic reservoirs that contain solutions used for microarray experiments. The system enables detection of microarray probes deposited on the microarray surface in parallel and in real-time. Sample preparation, microarray hybridization and probe/target detection are integrated with illumination of the microarray. The system provides a compact platform for detection applications, including portable sensing of bio-molecules (gene sequences, and proteins) from viruses, bacteria, plants, algae as well as eukaryotes (mammalian cells) or any experiment that could be accomplished on a microarray platform.

Microarray Preparation and Detection. Detection of a typical microarray is performed after the microarray is spotted and has been hybridized for approximately 12 hours. After this incubation period, the microarray is washed using several solutions and the probes or spots are illuminated with an excitation source (illuminator) and the emission from the microarray (fluorescent intensity of each probe or spot) is detected using a CCD detector. The system performs all of these steps with a single microfluidic chip. The system incorporates a microfluidic chip and hardware assemblies to perform sample preparation, hybridization and spot detection. Three elements of the system, fluidic handling, optical detection, and thermo control are further described below.

Fluidic Handling. Microfluidic microarray chips useful in the detection of biomoleculesare suitably described in U.S. pat. application Ser. No. 10/701,097, "Microfluidic Integrated Microarrays for Biological Detection", filed Nov. 4, 2003, the entirety of which is incorporated by reference herein. The system used in this example contained a fluid handling component to introduce, flush and remove fluids from the microfluidic chip. The fluid handling component, a manifold, was fabricated from DELRIN™ acetal resin (DuPont) and contains O-ring faced via holes designed to interface with microfluidic channels located on the microfluidic chip (FIG. 1). The microfluidic chip was placed into the manifold (FIG. 4) where the O-ringed via holes mated with the fluidic channels in the microfluidi chip was then secured to the manifold using a quartz backing plate (FIG. 5) and compression backing frame (FIG. 6). Once the chip was secured the fluidic connection to one or more capillaries was established. On the opposite side of the manifold, the manifold fluidic ports (elements 28 in FIG. 2) were connected with capillary fittings to the manifold for introducing buffers, solvents and samples to the fluidic microarray and sample prep channels located on the microfluidic chip.

The next step in the use of the microfluidic microarray is to seal the open channei microarray located on the surface of the microfluidic chip. Descriptions and uses of suitable microfluidic chips that contain an open channel microarray on the surface of the microfluidic chip, as well as deposition of biomolecules on the microarray, is further described in U.S. app. Ser. No. 10/701,097, the entirety of which is incorporated by reference herein. The open channel microarray is sealed with a semi- elastic plastic film (FIG. 7). The film closes the channels and the microarray to allow fluid flow therethrough. After the film has been placed on the surface of the open microarray, a compression plug (FIGS. 3 and 7) is placed on top of the film to provide a pressure tight seal between the film and the microfluidic chip. This system allows pressure flows exceeding 100 PSI through the microfluidic microarray for microarray hybridization and channel washing. An overall depiction of the system design is provided in FIG. 3.

Optical Detection. Detection of the deposited probes on a glass microarray is performed using a CCD microarray detector that has the ability to monitor many thousand small elements in parallel with resolution approaching 10 µm. The CCD detector is positioned proximate to the microarray surface to perform real-time imaging. Without being bound by a particular theory of operation, if the detection device is not close enough to the microarray surface, the fluorescence (which is used to interrogate the presence of an analyte) is difficult to resolve due to the hemispherical pattern of light emission from each individual spot. A detector that is too distant from the microarray surface would not be able to discriminate individual spots due to this light emission pattern. To detect individual spots with adequate resolution, collection of light from the microarray surface is performed as close to the microarray as possible.

The microarray surface was illuminated with a light source that excites targets on the microarray surface to fluoresce. Light emitting diodes (LED), which were used as an excitation light source, were optically coupled to light guides fabricated from glass fibers. The LEDs were smaller than about 5 mm in size and could be energized using a single 1.5 volt AA battery or by using any other type of stationary or portable power supply. The LEDs were coupled to a fiber bundle using an optical union that permitted a solder-less connection of an LED to the union. The opposite ends of the fiber bundles were formed into a rectangular shaped illuminator and were used to transmit excitation light to the microfluidic chip (FIGS. 4 and 8). This illuminator is compact and easily integrated with the fluidic manifold (FIG. 4). In this system the illuminator was mounted to the fluidic manifold by an aluminum mounting bar which is threaded to accept a positioning screw from the opposite side of the manifold (FIG. 8). This assembly transmits excitation light to the microfluidic microarray through the microfluidic chip (FIG. 4), the transparent backing plate (FIG. 5), or both. Once illuminated, fluorescent spots on the microarray are detected using a CCD detector. In other examples, fiber bundles were bifurcated to provide two excitation wavelengths to the chip. For example, two-color light was directed through a single bifurcated fiber bundle in which red (635 nm) light and blue (475 nm) light are individually guided through a bifurcated fiber bundle. When two-color detection is desired the power supply can be altered to alternate between wavelengths, which in this example appears as an overlapped pink hue color. The wavelengths selected in this example do not overlap, but alternate well within the fluorescent lifetime of the individual dyes used for target labeling. Fiber bundles can also be separated into three or more portions to provide light from three or more excitation sources. Other combinations of fiber bundles and lights sources can also be made.

Fluorescent targets hybridized to the microfluidic microarray are detected with a CCD that is coupled to a optical grade fiber bundle. Collection with adequate resolution can be accomplished using CCD arrays that are coupled to a fiber bundle that mates directly to the microarray surface. For the current device commercially available CCD arrays and tapered fiber bundles were used to detect the microarray probes. A standard 2:1 ratio tapered optic fiber bundle was used to image the microarray surface from either side (FIGS. 8 and 9). To detect spots with high resolution, the compression plug (FIGS. 3 and 7) is removed and replaced with the optic fiber bundle. The compression plug or the optic fiber bundle is compressed to the film to seal the surface of the microarray, thus forming a closed microarray channel. After the optic fiber bundle is mated to the microarray surface, the CCD detector is aligned to the optic fiber bundle. Images of the microarray surface can be collected and processed. The resulting image shows the spotted microarray surface. The fluorescence on the microarray surface is/was imaged in real-time. The image data is then saved on a laptop computer for further processing. When individual spots are detected, the spots can be identified (as specific genes or proteins) by spatial location. Software is developed to provide rapid interrogation of each probe location and intensity and to cpmpare these resulting intensities to contro probes which are deposited on the microarray.

Figure 11:
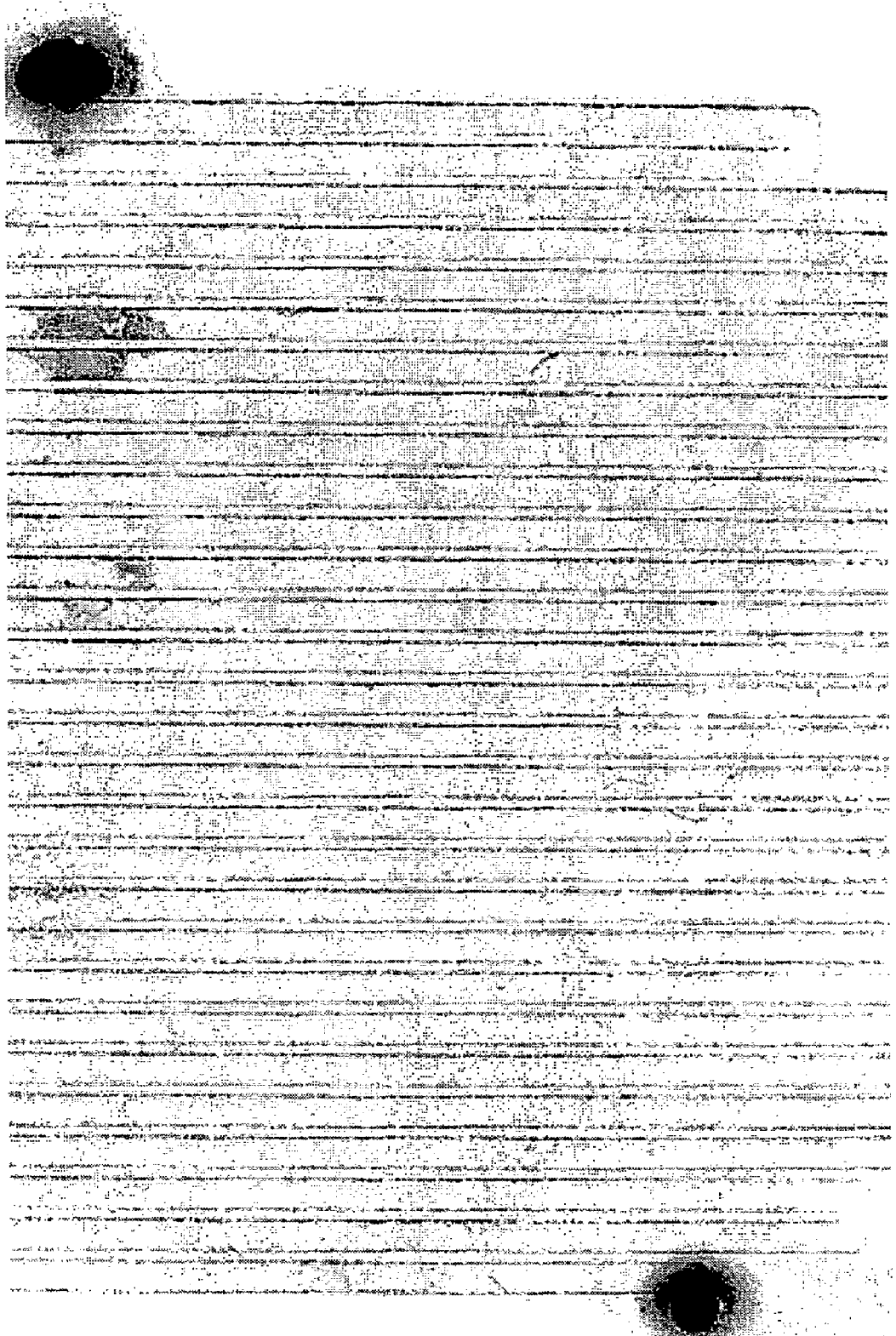
FIG. 11 is a bitmap screen image of a portion of a serpentine microarray using a system of the present invention.

FIG. 11 depicts a bitmap screen image of a portion of a serpentine microarray using the system described herein. A microfluidic chip having the serpentine microarray mounted in the system was illuminated with blue light from an illuminator coupled to both red and blue LEDs. A tapered optical fiber bundle was used to reduce the image by a factor of two. The reduced image (bright blue illuminated microarray channel edges on a dark background) was converted to the bitmap screen image using a CCD camera. Imaging software was used to invert the colors and convert to a gray scale image to depict dark microarray channel edges on a bright background. The dark spots indicate the location of the entrance and exit vias of the microarray channel. Microchannel dimensions are: width is about 300 microns, ridge (separation) of about 100 microns, depth about ten microns. The microfluidic chip containing a circular serpentine microarray was previously described in U.S. patent application Ser. No. 10/701,097, "Microfluidic Integrated Microarrays for Biological Detection", filed Nov. 4, 2003, the entirety of which is incorporated by reference herein.

The microarray surface is treated with hexanes and acetic acid and then with a silane functionalized epoxide rings. Amine-tagged oligonucleotide probes are subsequently attached to the treated surface of the microarray. The microarray is spotted with a fluorescently labeled oligonucleotide. Oligonucleotides (e.g., oligo-dT) of approximately 30 base pairs can be fluorescently labeled with FITC (Fluorescein), CY3 and CY5, and are commercially available from Molecular Probes, Eugene, Oreg. CY3 emits at about 575 min and CY5 emits at about 675 nm. A red LED illumination source is used to excite CY5 and a blue LED illumination source is used to excite FITC. A 500-550 nm illumination source will excite CY3. Oligonucleotide probes for various organisms are commercially available.

Spotting of oligonucleotide probes to the microfluidic microarray chips is achieved by use of a robotic spotter that spots the probes in a custom addressable array. The robotic spotter has micron resolution to position the spotting pens within the microchannels. Further details of robotic spotting are provided in U.S. patent application Ser. No. 10/701,097, "Microfluidic Integrated Microarrays for Biological Detection", filed Nov. 4, 2003, the entirety of which is incorporated by reference herein. After spotting, the microfluidic chip is cleaned and prepped following standard procedures (0.1% sarcosine, next 3×SSC, rinse in deionized water, and immersion in ice cold ethanol). Sample oligonucleotide probes, for example commercially-available rat DNA probes from MWG Biotech (High Point, N.C.) are attached to the microarray surface according to these processes.

A system including a serpentine microarray microfluidic chip is mounted to a manifold using O-ring face seals for maintaining the entrance and exit fluidic connections. The microarray is sealed using pressure or adhesion with an optically transparent chemically resistant plastic film. The microarray can be adhesively sealed by treating a chemically resistant clear plastic sheet (e.g., PDMS, polycarbonate, PMMA and various polyolefins) with plasma oxidation to activate surface functional groups. Amine-tagged silane is used to treat oxygen groups on the surface of the plastic film. The plastic surface is then bound to the top surface of the microfluidic chip, including the ridges between the microarray microchannels, using compression at 90° C. for about five minutes. The fiber bundle is placed on the plastic film, and the CCD camera is placed adjacent to the fiber bundle for imaging the microarray. At least one of the surfaces of the CCD, the plastic film, or the fiber bundle optionally may include one or more optical filters.

Hybridization is carried out on the sealed, probe-spotted, microarray by flowing a dilute sample containing fluorescently labeled mRNAs in a hybridization buffer into the microchannel microarray at about 5 to 10 microliters per minute for about 20 minutes. Sample flow is carried out using a syringe that is coupled to the chip through the manifold, and excess sample exits the chip through an exit via. Sample mRNAs can be extracted and fluorescently labeled using standard laboratory procedures or by using the extraction monoliths as described in U.S. patent application Ser. No. 10/701,097, "Microfluidic Integrated Microarrays for Biological Detection", filed Nov. 4, 2003, the entirety of which is incorporated by reference herein. Hybridization is carried out under flow conditions at about 42° C. for about 20 minutes. Heating is achieved using a TEC. Flow of fluorescently-labeled sample is ceased, excess sample is flushed away, and the microarray is imaged. The location of the fluorescence on the microarray is correlated to a particular probe, which is used to identify the biological origin of the sample. Optionally, SYBR GREEN (Qiagen, Inc., Valencia, Calif.) is added to the unlabeled mRNA sample, which fluoresces on the probe when hybridization occurs, thereby enabling imaging real time hybridization without requiring flushing of the fluorescently-tagged sample.

Temperature control. Thermal control of the microarray surface provides appropriate temperatures for conducting efficient target/probe hybridization. A commercially available thermoelectric cooler (TEC) capable of rapid heating and cooling is placed adjacent to the microfluidic chip (FIG. 10). The TEC replaces the transparent backing plate (FIG. 5) and resides between the compression backing plate and the microfluidic chip (FIG. 10). The TEC is connected to a power supply and a temperature control board.

Methods, materials and devices for making and using systems incorporating a manifold in fluid communication with a microfluidic chip comprising a microarray, an illuminator, and a detector in optical communication with the microarray have been provided. While the present invention has been described in connection with the exemplary embodiments of the various figures and examples, it is to be understood that other similar embodiments may be used or modifications and additions may be made to the described embodiments for performing the same function of the present invention without deviating therefrom. For example, one skilled in the art will recognize that the systems of the present invention as described in the present application may include, for example, additional components, or components that provide an equivalent function yet are shaped differently. Likewise, the microfluidic chips as described in the present application may include, for example, any combination of a plurality of microfluidic structures, a plurality of vias, or both, which are fluidically coupled to the manifold to achieve sample preparation, coupling and detection of biomolecules. In addition, the methods of the present invention may include additional processing steps, for example, on-chip PCR and hybridization. Therefore, the present invention should not be limited to any single embodiment, but rather should be construed in breadth and scope in accordance with the appended claims.

What is claimed:

1. A system, comprising:
a manifold comprising an opening disposed through the manifold, a recessed portion disposed about the opening in one surface of the manifold, the recessed portion for receiving a microfluidic chip, first and second lateral slots for providing light access to opposite edges of the microfluidic chip, means for securing the microfluidic chip to the manifold, and a plurality of via holes in fluid communication with a plurality of microchannels disposed on the microfluidic chip, the microfluidic chip comprising a microarray, the microfluidic chip capable of receiving and transmitting light to the microarray;
an illuminator for providing the light; and
a detector in optical communication with the microarray.

2. The system of claim 1, wherein the microfluidic chip is secured to the manifold using a backing plate and a compression frame.

3. The system of claim 2, wherein the backing plate is optically transparent.

4. The system of claim 2, wherein the backing plate comprises diamond, quartz, glass, ceramic, silicon or plastic.

5. The system of claim 1, wherein the microfluidic chip is optically transparent.

6. The system of claim 1, wherein the manifold further comprises at least one port in fluid communication with at least one fluid source.

7. The system of claim 6, wherein the fluid source comprises buffer, solvent, sample, analyte, probe, label, tag, salts, acids, bases, detergents, or any combination thereof.

8. The system of claim 1, wherein the plurality of microchannels comprise open microchannels disposed on a surface of the microfluidic chip.

9. The system of claim 1, wherein the microarray is in fluid communication with at least one of the microchannels.

10. The system of claim 1, wherein the microarray comprises a plurality of biomolecules.

11. The system of claim 2, wherein the microfluidic chip is fluidically sealed to the backing plate.

12. The system of claim 1, wherein the detector comprises a microscope, scanner, PMT, CCD, or any combination thereof.

13. The system of claim 1, wherein the microarray comprises a plurality of biomolecular spots disposed on the microarray.

14. The system of claim 1, further comprising an optical coupling situated between the microfluidic chip and the detector.

15. The system of claim 14, wherein the optical coupling comprises an optical waveguide, a lens, an optical fiber bundle, a glass or plastic rod, a fiber plate, an aperture, or any combination thereof.

16. The system of claim 15, wherein the detector comprises a plurality of pixels, and wherein at least a portion of the pixels are optically coupled to a plurality of biomolecular spots disposed on the microarray.

17. The system of claim 16, wherein each of the pixels are, independently, optically coupled to one biomolecular spot.

18. The system of claim 13, wherein at least a portion of the biomolecular spots are capable of binding an analyte.

19. The system of claim 18, wherein the analyte comprises a fluorophore, a chromophore, or any combination thereof.

20. The system of claim 19, wherein a photon emitted from the fluorophore or chromophore is detected by the detector.

21. The system of claim 20, wherein a photon emitted from the fluorophore or chromophore is optically communicated to a pixel on the detector.

22. The system of claim 1, wherein the illuminator comprises a waveguide.

23. The system of claim 22, wherein the waveguide comprises a fiber bundle.

24. The system of claim 1, wherein the illuminator comprises an LED, an incandescent light source, a fluorescent light source, an electroluminescent light source, a plasma light source, a laser, or any combination thereof.

25. The system of claim 1, further comprising a temperature controller.

26. The system of claim 1, wherein the microfluidic chip comprises a surface and features formed in the surface, wherein at least a portion of the surface of the microfluidic chip is fluidically sealed to a substrate.

27. The system of claim 26, wherein the substrate comprises a film.

28. The system of claim 27, wherein the film is compressibly sealed to the microfluidic chip.

29. The system of claim 28, wherein the film comprises a semi-elastic plastic material.

30. The system of claim 28, wherein the film compressibly sealed to the microfluidic chip surface forms structures capable of containing and transporting fluids.

* * * * *

UNITED STATES PATENT AND TRADEMARK OFFICE
CERTIFICATE OF CORRECTION

| | |
|---|---|
| PATENT NO. | : 7,524,672 B2 |
| APPLICATION NO. | : 10/946920 |
| DATED | : April 28, 2009 |
| INVENTOR(S) | : Jay A. A. West, Kyle W. Hukari and Gary A. Hux |

It is certified that error appears in the above-identified patent and that said Letters Patent is hereby corrected as shown below:

IN COL. 2, LINE 8: the word "anda" AFTER the words and punctuation "the light;" and BEFORE the words "detector in optical communication" is misspelled and should be DELETED and REPLACED with the words --and a--.

IN COL. 3, LINE 37: the word "ijiuminating" AFTER the words "light for" and BEFORE the words and punctuation "the microarray, which is in optical" is misspelled and should be DELETED and REPLACED with the word --illuminating--.

IN COL. 6, LINE 10: the words "everjn" at the beginning of the line BEFORE the words and punctuation "preferred embodiments," is misspelled and should be DELETED and REPLACED with the words --ever in--.

Signed and Sealed this

Seventh Day of July, 2009

JOHN DOLL
*Acting Director of the United States Patent and Trademark Office*